(12) United States Patent
Yoshida et al.

(10) Patent No.: US 6,862,532 B2
(45) Date of Patent: Mar. 1, 2005

(54) APPARATUS FOR MANIFESTING LATENT CHARACTERISTICS EXISTING IN SEQUENCES OF SYMBOLS

(75) Inventors: Tetsuhiko Yoshida, Nagoya (JP); Kenji Oosawa, Nara (JP); Nobuaki Obata, Nagoya (JP)

(73) Assignee: TOA Gosei Kabushiki Kaisha, Tokyo (JP)

( * ) Notice: Subject to any disclaimer, the term of this patent is extended or adjusted under 35 U.S.C. 154(b) by 365 days.

(21) Appl. No.: 10/137,402

(22) Filed: May 3, 2002

(65) Prior Publication Data

US 2002/0172971 A1 Nov. 21, 2002

Related U.S. Application Data

(62) Division of application No. 09/137,162, filed on Aug. 20, 1998, now Pat. No. 6,438,496.

(30) Foreign Application Priority Data

Aug. 20, 1997 (JP) .............................. 9-223908

(51) Int. Cl.[7] .......................... G01N 33/48; C12Q 1/68
(52) U.S. Cl. ............................. 702/19; 435/6
(58) Field of Search ............................... 702/19; 435/6

(56) References Cited

PUBLICATIONS

Doron Witztum, et al., "Equidistant Letter Sequences in the Book of Genesis", Statistical Science, vol. 9, No. 3, (1994), pp. 429–438.
Dear et al., Nucleic Acids Research, vol. 19, No. 14, pp. 3907–3911, (1991).
Yoshida et al., "Color–Coding Reveals Tandem Repeats in the *Escherichia coli* genome", J. Mol.. Biol. 298, 343–349 (2000).
Obata et al., "A Method for Information Analysis of Sequences by Two–Dimensional Patter Formation With Coloration, "Scientific Research From Ministry of Education, Japan, No. 09874043 and No. 09878140, (1997).
Lipman et al., "Rapid and Sensitive Protein Similarity Searches", Science, vol. 227, pp. 1435–1441, Mar. 22, 1985.
Altschul et al., "Basic Local Alignment Search Tool", J. Mol. Biol. (1990) 215, 403–410.
Baldi et al., "Hidden Markov Models of Biological Primary Sequence Information", Proc. Natl. Acad. Sci. US. vol. 91, pp. 1059–1063, Feb. 1994.
Maizel et al., "Enhanced Graphic Matrix Analysis of Nucleic Acid and Protein Sequences" Proceedings of the National Academy of Sciences of the USA, US, New York, NY, vol. 78, No. 12, Dec. 1, 1981, pp. 7665–7689, XP002038657 *p. 7686, Right Hand Column, Line 57–62 *p. 7666, Right–Hand Column, Line 19–21.
X. Guan et al., "A Fast Look–Up Algorithm for Detecting Repetitive DNA Sequences" Jan. 6, 1996, World Scientific, San Francisco, USA XP000953382 "The Whole Document".
Thompson et al., Nucleic Acids Research, vol. 22, No. 22, pp. 4673–4680 (1994).
Hiromitsu Yokoo et al., ICARUS, 38, 148–153 (1979), "Is Bacteriophage φX174 DNA a Message from an xtraterrestrial Intelligence?".

*Primary Examiner*—Ardin H. Marschel
(74) *Attorney, Agent, or Firm*—Oblon, Spivak, McClelland, Maier & Neustadt, P.C.

(57) ABSTRACT

A computer processor converts a symbolic sequence $I_j$ (j=1~m) into a parallel sequence A(k), in which the suffix j is aligned in the following positional relationship:

| | | | |
|---|---|---|---|
| j = 1, | 2, . . . | k − 1, | k |
| j = k + 1, | k + 2, . . . | k + k − 1, | k + k |
| : | | | |
| j = (n − 1)k + 1, | (n − 1)k + 2, . . . | (n − 1)k + k − 1, | (n − 1)k + k |
| j = nk + 1, | nk + 2, . . . | nk + k − 1, | nk + k | and additional parallel sequences A(k) can be generated by changing k to p, p+r, p+2r, p+3r . . . . Therefore, a set of parallel sequences ΣA(k) can be generated. The parallel sequences may then be visually displayed using different colors for the different symbols in order to reveal at least one latent characteristic existing in the symbolic sequence $I_j$.

20 Claims, 18 Drawing Sheets

| | k=2 | k=3 | k=4 | k=20 |
|---|---|---|---|---|
| 1 | 1 2 | 1 2 3 | 1 2 3 4 | 1 2 3 ··· 20 |
| 2 | 3 4 | 4 5 6 | 5 6 7 8 | 21 · · · · |
| 3 | 5 6 | 7 8 9 | 9 10 11 12 | |
| 4 | 7 8 | 10 11 12 | 13 14 15 16 | |
| 5 | 9 10 | 13 14 15 | 17 18 19 20 | · · · · · 100 |
| 6 | 11 12 | 16 17 18 | · · · · | |
| 7 | 13 14 | 19 20 · | · · · · | |
| 8 | 15 16 | · · · | · · · · | |
| 9 | 17 18 | · · · | | |
| 10 | 19 20 | · · · | | |
| 11 | · | | | |
| 12 | · | | | |
| 13 | · | | | |
| 14 | | | | |
| 15 | | | | |
| 16 | | | | |
| 17 | | | | |
| 18 | | | | |
| 19 | | | | |
| 20 | | | | |

FIG.10 q = 5

| | k = 2 | k = 3 | k = 4 | | k = 6 |
|---|---|---|---|---|---|
| 1 | 5 10 | 5 10 15 | 5 10 15 20 | | 5 10 15 20 25 30 |
| 2 | 15 20 | 20 25 30 | 25 30 35 40 | | 35 40 45 50 55 60 |
| 3 | 25 30 | 35 40 45 | 45 50 55 60 | · · | 65 70 75 80 85 90 |
| 4 | 35 40 | 50 55 60 | 65 70 75 80 | | 95 |
| 5 | 45 50 | 65 70 75 | 85 90 95 | | |
| 6 | 55 60 | 80 85 90 | | | |
| 7 | 65 70 | 95 | | | |
| 8 | 75 80 | | | | |
| 9 | 85 90 | | | | |
| 10 | 95 | | | | |
| 11 | | | | | |
| 12 | | | | | |
| 13 | | | | | |
| 14 | | | | | |
| 15 | | | | | |
| 16 | | | | | |
| 17 | | | | | |
| 18 | | | | | |
| 19 | | | | | |
| 20 | | | | | |
| . | | | | | |
| . | | | | | |
| . | | | | | |

FIG.12

| | k=2 | k=3 | k=4 | k=20 |
|---|---|---|---|---|
| 1 | 1  2 | 1  2  3 | 1  2  3  4 | 1  2  3  · · ·  20 |
| 2 | 4  3 | 6  5  4 | 8  7  6  5 | · · ·  22  21 |
| 3 | 5  6 | 7  8  9 | 9  10  11  12 | |
| 4 | 8  7 | 12  11  10 | 16  15  14  13 | |
| 5 | 9  10 | 13  14  15 | 17  18  19  20 | · · · · · 100 |
| 6 | 12  11 | 18  17  16 | · · · · | |
| 7 | 13  14 | 19  20  · | · · · · | |
| 8 | 16  15 | · · · | · · · · | |
| 9 | 17  18 | · · · | | |
| 10 | 20  19 | · · · | | |
| 11 | · | | | |
| 12 | · | | | |
| 13 | · | | | |
| 14 | | | | |
| 15 | | | | |
| 16 | | | | |
| 17 | | | | |
| 18 | | | | |
| 19 | | | | |
| 20 | | | | |

FIG.16

APPARATUS FOR MANIFESTING LATENT CHARACTERISTICS EXISTING IN SEQUENCES OF SYMBOLS

CROSS-REFERENCE

This application is a divisional application of U.S. patent application Ser. No. 09/137,162, now U.S. Pat. No. 6,438,496 filed Aug. 20, 1998 which application claims priority to Japanese patent application serial number 9-223908.

BACKGROUND OF THE INVENTION

1. Field of the Invention

The present invention relates to methods and apparatus for manifesting a characteristic or regularity, which is latent and can not ordinarily be recognized by visual inspection, although such characteristic or regularity actually exists in a complicated symbolic sequence, for example, a nucleotide sequence of DNA, an amino acid sequence of a protein, or a digital sequence of decimal expansion of an irrational number and the like. In these sequences, regularity can not be recognized at a glance even when regularity exists therein. The present invention enables recognition of a characteristic or regularity existing within a symbolic sequence, which has not yet been recognized.

2. Description of the Related Art

Some complicated symbolic sequences contain a characteristic, which has not been recognized by human beings, although the characteristic actually exists. For example, genetic information is represented by a long sequence of symbols. The symbols consist of four different symbols, each indicating one of the four types of nucleotides. A large number of symbols are one-dimensionally aligned. In the study of genetic information, it is extremely important to recognize a certain regularity hidden within the symbolic sequence that represents the genetic information. In addition, if a certain regularity is found in an irrational number, e.g., the number $\pi$, and the base of natural logarithm (e), the study of irrational numbers will be enhanced and various developments can be expected in mathematics.

For such purpose, various efforts have been made to analyze a symbolic sequence based on a variety of mathematical methods, such as Fourier analysis. However, these efforts have not necessarily accomplished successful results. One problem with conventional analysis methods is that, even if a certain regularity exists within a portion of a very long symbolic sequence, the latent regularity is buried within the entire sequence and can not be recognized when the entire symbolic sequence is analyzed. Since there has been no effective technology for determining in advance as to which part of the sequence that the regularity exists, there are many characteristics or regularity which can not be recognized by conventional analysis methods.

SUMMARY OF THE INVENTION

An object of the present invention is to provide methods and apparatus which manifest a characteristic or regularity even if such characteristic or regularity exists only in a portion of the entire symbolic sequence, and thereby enable recognition of a characteristic or regularity which has not been previously recognized.

Another object of the present invention is to manifest a characteristic or regularity existing throughout the entire sequence.

In one embodiment of the present invention, a symbolic sequence $I_j(j=1\sim m)$ is converted into a parallel sequence A(k) of partial symbolic sequences, in which the suffix j is aligned in the following positional relationship:

| | | | |
|---|---|---|---|
| j = 1, | 2, ... | k − 1, | k |
| j = k + 1, | k + 2, ... | k + k − 1, | k + k |
| : | | | |
| : | | | |
| j = (n − 1)k + 1, | (n − 1)k + 2, ... | (n − 1)k + k − 1, | (n − 1)k + k |
| j = nk + 1, | nk + 2, ... | nk + k − 1, | nk + k. |

In the alternative, the positional relationship may be represented as follows:

| | | | |
|---|---|---|---|
| j = 1, | 2, ... | k − 1, | k |
| j = k + k, | k + k − 1, ... | k + 2, | k + 1 |
| : | | | |
| j = (n − 1)k + k, | (n − 1)k + k − 1, ... | (n − 1)k + 2, | (n − 1)k + 1 |
| j = nk + 1, | nk + 2, ... | nk + k − 1, | nk + k. |

Herein, k represents an integer of 2 or more, n represents an integer such that $nk<m\leq nk+k$, and when the suffix j is m+1 or more, the result is ignored.

Then, the converted parallel sequence A(k) is output using one or more means for expressing the output selected from color hue, color lightness and color saturation and from sound interval, sound tone and sound volume.

"Equidistant Letter Sequences in the Book of Genesis" (Doron Witztum, Eliyahu Rips and Yoav Rosenberg, Statistical Science 1994, Vol. 9, No. 3, page 429–438) introduces a technology in which a code hidden in a one-dimensional letter sequence is decoded by converting the one-dimensional letter sequence into a parallel sequence A(k) of partial symbolic sequences. In this known technology, words having meanings must be extracted from the parallel sequence A(k) of partial symbolic sequences, and this known method can not be used for sequences other than letter sequences. Further, when searching for a certain regularity in a symbolic sequence, which symbolic sequence appears to be irregular at a glance and which is often the case in the fields of natural science, inconsistency, (i.e., regularity can not be recognized unless the regularity has been identified in advance), can not be solved.

In the present invention described above, since a parallel sequence A(k) of partial symbolic sequences is output using one or more expression means selected from color hue, color lightness and color saturation and from sound interval, sound tone and sound volume, even if the regularity is not known in advance, that regularity is manifested by a pattern of color hue, color lightness or color saturation or sound interval, sound tone or sound volume and can be easily recognized.

In another embodiment of the present invention, a one-dimensional symbolic sequence $I_j(j=1\sim m)$ is converted into a parallel sequence A(k) of partial symbolic sequences, in which the suffix j is aligned in the following positional relationship:

| | | | |
|---|---|---|---|
| j = 1, | 2, ... | k − 1, | k |
| j = k + 1, | k + 2, ... | k + k − 1, | k + k |

-continued

| | | | |
|---|---|---|---|
| ⋮ | | | |
| j = (n − 1)k + 1, | (n − 1)k + 2, ... | (n − 1)k + k − 1, | (n − 1)k + k |
| j = nk + 1, | nk + 2, ... | nk + k − 1, | nk + k. |

In the alternative, the positional relationship may be represented as follows:

| | | | |
|---|---|---|---|
| j = 1, | 2, ... | k − 1, | k |
| j = k + k, | k + k − 1, ... | k + 2, | k + 1 |
| ⋮ | | | |
| j = (n − 1)k + k, | (n − 1)k + k − 1, ... | (n − 1)k + 2, | (n − 1)k + 1 |
| j = nk + 1, | nk + 2, ... | nk + k − 1, | nk + k. |

Further, when p represents a natural number from 2 to less than m, r represents any natural number, the above-described conversion is repeated by changing k to p, p+r, p+2r, p+3r, ... in order to obtain parallel symbolic sequences of partial symbolic sequences: A(p), A(p+r), A(p+2r), A(p+3r) ... Then, the resulting parallel sequences: A(p), A(p+r), A(p+2r), A(p+3r) ... are further parallel-positioned in order to generate a set of parallel sequences ΣA(k). Then, the set of parallel sequences ΣA(k) is output. Herein, n represents an integer such that nk<m≦nk+k, and when the suffix j is m+1 or more, the result is ignored.

In this case, a parallel sequence generated by parallel-positioning p partial symbolic sequences, a parallel sequence generated by parallel-positioning p+r partial symbolic sequences, and parallel sequences generated by parallel-positioning of similar increasing numbers of partial symbolic sequences, are all parallel-positioned. In this processing, if regularity of period length α is hidden in the symbolic sequence, such regularity is remarkably manifested in a parallel sequence A(α) generated by parallel-positioning of partial symbolic sequences of a number of α.

If α falls within p, p+r, p+2r, p+3r, ... rows, the regularity having period length α is manifested in a parallel sequence of partial symbolic sequences of an analogous number to α. Therefore, increment r regarding the number of the partial symbolic sequences is not necessarily required to be one, and it may advantageously be any natural number. In this case, when the increment r is smaller, the characteristic is more easily manifested.

In this embodiment, regularity of an unknown period length is manifested in a parallel sequence of partial symbolic sequences of some number, and recognition of the characteristic becomes easy.

In the above-described method, each symbol is preferably expressed by a combination of color hue, color lightness and color saturation. In this embodiment, as a result of the manifestation of the characteristic hidden in the symbolic sequence through visual means, a more comprehensive understanding of the characteristic hidden in the symbolic sequence is possible, and various applications and developments utilizing the characteristic are made possible. Further, the resulting visual pattern is a pattern including mixed regularity and irregularity that was not previously known, and a visual pattern of which design itself has utility can be designed.

Each symbol may be expressed by a combination of sound interval, sound tone and sound volume. By expressing the parallel sequence as a combination of sound interval, sound tone and sound volume, a unique audio pattern is created and the characteristic of the symbolic sequence can be recognized through auditory means.

One symbol may be removed from the original symbolic sequence at an interval of k-1 (namely, at every k) in order to generate a symbolic sequence. The present method is then applied to this extracted symbolic sequence. If a regularity of period length k is hidden in the original symbolic sequence, the regularity is manifested and appears remarkably.

One symbol may be removed from the original symbolic sequence at an interval of kq-1 (namely, at every kq) in order to generate a symbolic sequence. The present method is then applied to this extracted symbolic sequence. If a regularity of period length kq is hidden in the original symbolic sequence, the regularity is manifested and appears remarkably.

Further, when any of the above-described methods are conducted by changing k to p, p+r, p+2r ..., a set of parallel sequences ΣA(k) is generated, including a parallel sequence A(p) generated by parallel-positioning p partial symbolic sequences, a parallel sequence A(p+r) generated by parallel-positioning p+r partial symbolic sequences, and parallel sequences generated by parallel-positioning similar increasing numbers of partial symbolic sequences. A regularity of period length α appears remarkably in a parallel sequence A(α) formed by parallel-positioning of k (=α) partial symbolic sequences. Therefore, a characteristic or regularity of unknown period length is manifested, and recognition of the characteristic or regularity becomes easy.

According to this method, even if the period length α of regularity or characteristic exists between p, p+r, p+2r, ... rows, the characteristic or regularity is manifested in a parallel sequence formed by parallel-positioning partial sequences of a number approximately equal to α, and increment r is not necessarily required to be one. Therefore, the characteristic may be manifested using small amounts of data processing by selecting increment r according to the particular situation.

Further, by outputting the analyzed results using color and/or sound, expressions suitable for the particular situation and observer become possible, and the characteristic can be more easily recognized. The resulting color and/or sound pattern will be an interesting pattern in which regularity and irregularity are mixed, and the present method also can be utilized as a designing method.

In particular, when the initiation point of regularity is situated at an analysis initiation position, a pattern having a parabolic shape clearly appears, and a regularity having a long period length is manifested clearly, within the set of parallel sequences ΣA(k).

The present invention will be recognized more successfully by reading the descriptions of the following examples with reference to the drawings.

BRIEF EXPLANATION OF THE DRAWINGS

FIG. 10 depicts the conversion of a symbolic sequence having 100 symbols into a set of parallel sequences ΣA(k).

FIG. 12 depicts another example of converting a symbolic sequence into a set of parallel sequences ΣA(k).

FIG. 16 shows another positioning (reciprocal) pattern for generating a parallel sequence A(k).

DETAILED DESCRIPTION OF THE PREFERRED EMBODIMENTS

Experimental examples embodying the present invention will be described below.

Figure 1:
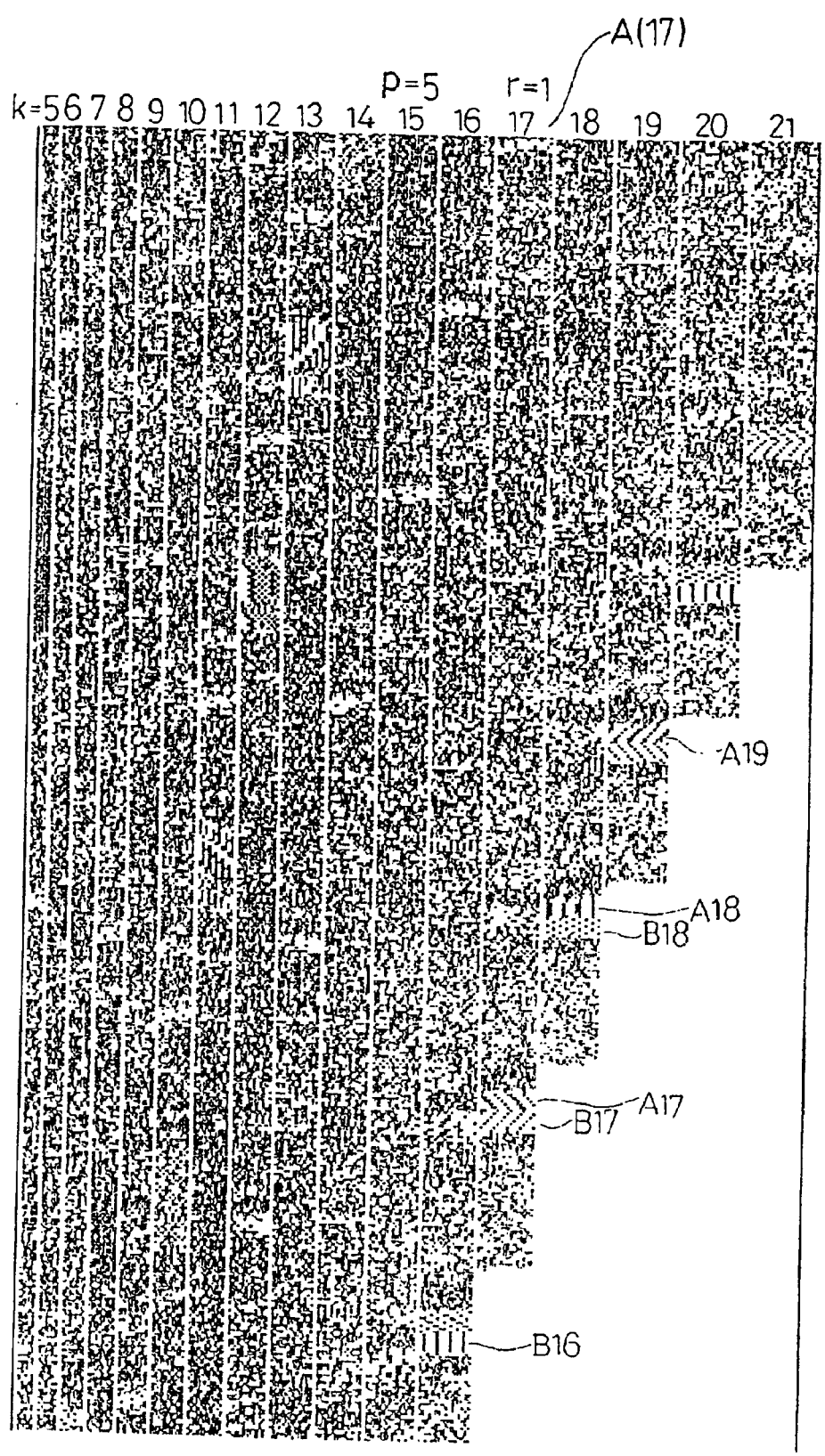
FIG. 1 shows a set of parallel sequences ΣA(k) generated from a nucleotide sequence of human genomic DNA.

FIG. 1 represents an experimental example for processing a symbolic sequence $I_j$ that represents a nucleotide sequence of human genomic DNA. A symbolic sequence $I_j$ representing the nucleotide sequence of human genomic DNA is typically represented as a one-dimensional sequence of an enormous number of symbols, each symbol indicating one of the four types of nucleotides (i.e., ATGC), and a certain regularity hidden therein is recognized as useful information. Therefore, it is an important object of genetic study to find regularity, or to identify a portion of the sequence that includes the regularity.

FIG. 1 represents a processed result output using color, and the four types of symbols (ATGC) are, respectively, expressed by four different colors, i.e., red, blue, green and yellow. Thus, FIG. 1 is expressed using four colors. Further, FIG. 1 represents the result when the present method is performed using the parameters of p=5 and r=1.

Figure 2:
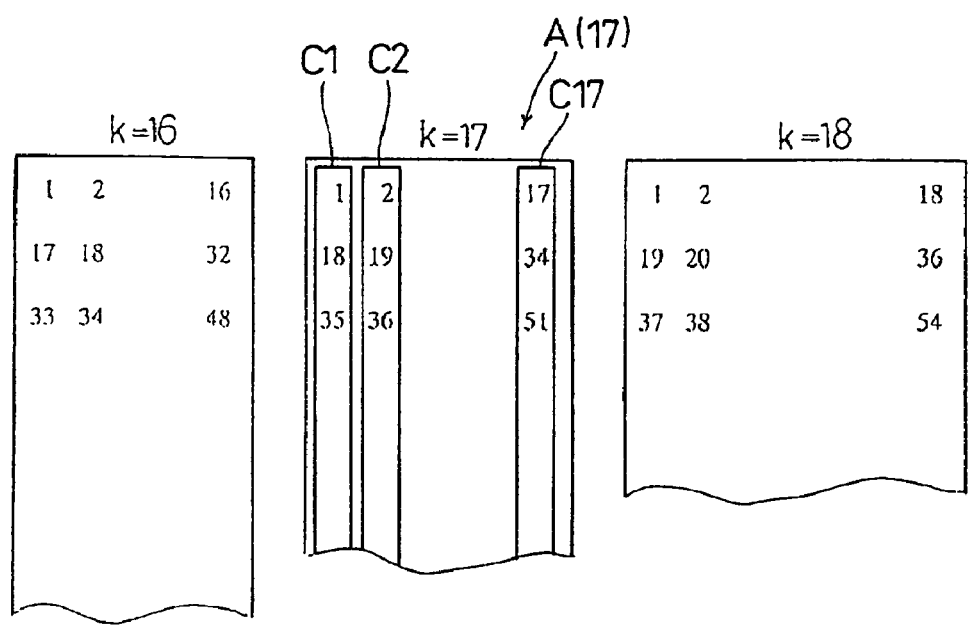
FIG. 2 depicts the positional relationship of suffix j in FIG. 1.

An example of a parallel sequence A(17) in which k=17 is shown in FIG. 2, in which longitudinal partial symbolic sequences C1, C2, C3 . . . C17 are extracted from a symbolic sequence $I_j$ at every k and aligned longitudinally. Then, the longitudinal sequences are laterally aligned to form a parallel sequence A(17). In columns C1, C2, C3 . . . , the values of symbol suffixes j that will be extracted are shifted by one. This rule is common to all k values and to all partial symbolic sequences C.

In this example, a symbol group extracted at every k is placed longitudinally (i.e., in columns) to form a longitudinal partial symbolic sequence, and the longitudinal partial symbolic sequences are laterally placed. However, the longitudinal to lateral relationship may be reversed, and a symbol group extracted at every k may be placed laterally to form a lateral partial symbolic sequence, and the lateral partial symbolic sequences may be longitudinally placed.

In FIG. 1, B16 remarkably shows that a repeating pattern having a period length of 16 exists in a portion of the nucleotide sequence. Based upon the pattern B16, one can learn that there is a possibility that useful information exists in this portion, and this portion is an area that is valuable for detailed analysis. B17 and B16 represent the same regularity. The regularity of period length 16 appears as vertical stripes in B16, and appears as inclined stripes in B17. The inclined stripes in B17 form a pattern that declines towards the left side. B18 also represents the same regularity, and the inclination of the stripes in B18 is closer to horizontal than in B17. The same regularity is also shown in a parallel sequence A(19) in which k=19. However, in this case, the inclination is almost horizontal, and extraction of characteristic becomes increasingly difficult.

Regularity of period length α appears vertically and is expressed most remarkably in A(α) in which k (=α) partial symbolic sequences are parallel-positioned. However, the regularity also appears in a parallel sequence of partial symbolic sequences in which k=α+1 and k=α+2. Therefore, it is confirmed that the increment r is not necessarily required to be 1.

A18 shows regularity of period length 18, and the same regularity is shown as pattern A17 and the parallel sequence A(17) in which k=17 declines towards the rights side, and shown as pattern A19 and the parallel sequence A(19) in which k=19 declines towards the left side.

In addition, many remarkable patterns appear in FIG. 1, and characteristics hidden in a nucleotide sequence of human genomic DNA can be recognized from these patterns.

The initial number p in the set of parallel sequences of partial symbolic sequences may be any natural number, and in FIG. 1, p=5. The increment r is not limited to 1, and it may be 2 or more. When r is smaller, characteristics always can be found, and when r is larger, data processing is reduced. The increment r is not required to be constant, and it is preferable to select the increment r according to the particular situation.

Figure 18:
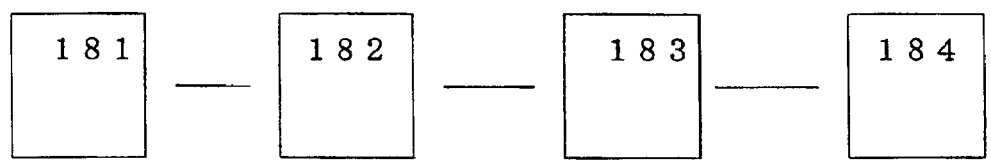
FIG. 18 represents an apparatus for performing the methods of the present invention.

FIG. 18 represents an apparatus for performing the above-described processing method, and in this apparatus, a symbolic sequence $I_j$ that will be analyzed is stored in memory apparatus 181. Apparatus 182 converts the symbolic sequence Ij into a parallel sequence A(k), apparatus 183 generates the set of parallel sequences ΣA(k) in which a plurality of parallel sequences A(k) obtained by changing the value of k are parallel-positioned, and apparatus 184 outputs the set of parallel sequences ΣA(k). Apparatus 182 and 183 may be a computer and apparatus 184 may be a color printer. When the set of parallel sequences ΣA(k) is output using sound, a sound synthesizer may be used as apparatus 184.

FIG. 1 is preferably expressed with a time lapse according to processing speed of the symbolic sequence. For example in FIG. 1, color corresponding to I1 is first expressed on the left upper summits of A(5) to A(21), and the further expressions of I2, I3, I4 . . . are effected in succession. By using this change in time, characteristics are more easily recognized, and also in the case of output by sound, output with a time lapse is effective. When output with a time lapse is conducted, characteristics are recognized using the changes in sound.

Figure 3:
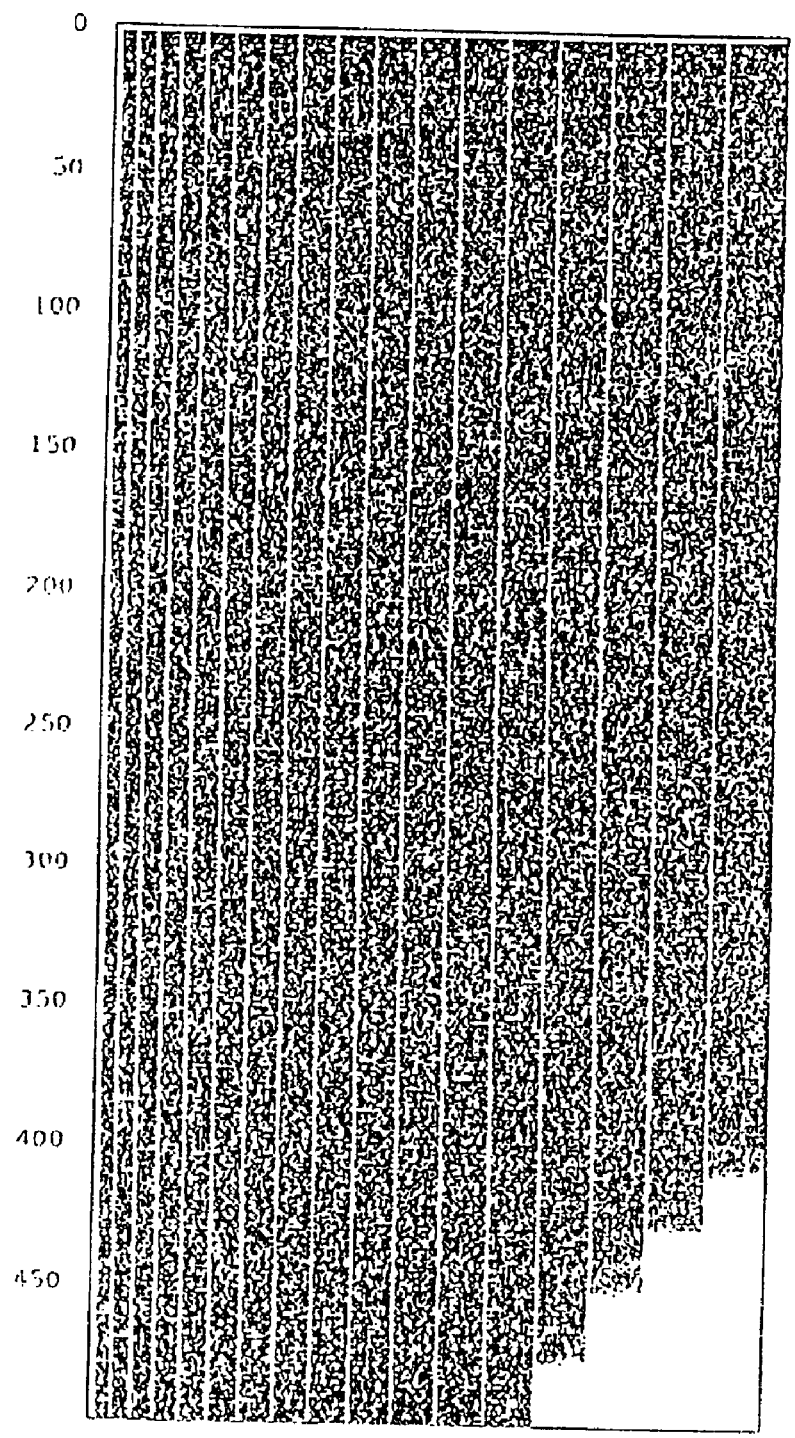
FIG. 3 shows a set of parallel sequences ΣA(k) generated from a numerical sequence π.

FIG. 3 exemplifies a result obtained by processing the symbolic sequence of π(i.e., the numerical sequence), and the 10 symbols (i.e., numbers 0 to 9) are expressed using 10 equally divided colors within the spectrum from a violet to red. FIG. 3 shows that specific symbols (numbers) tend to appear frequently within a specific range.

When noise input is processed as a row of a symbolic sequence and this symbolic sequence is processed to obtain a similar pattern as in FIG. 3, it becomes possible to extract a characteristic existing in the noise and to extract only meaningful sound included in the noise. Further, it is known that the pattern shown in FIG. 3 can be used, for example, as a ground pattern for securities, and this complicated ground pattern can be specified by a one-dimensional symbolic sequence.

Figure 4:
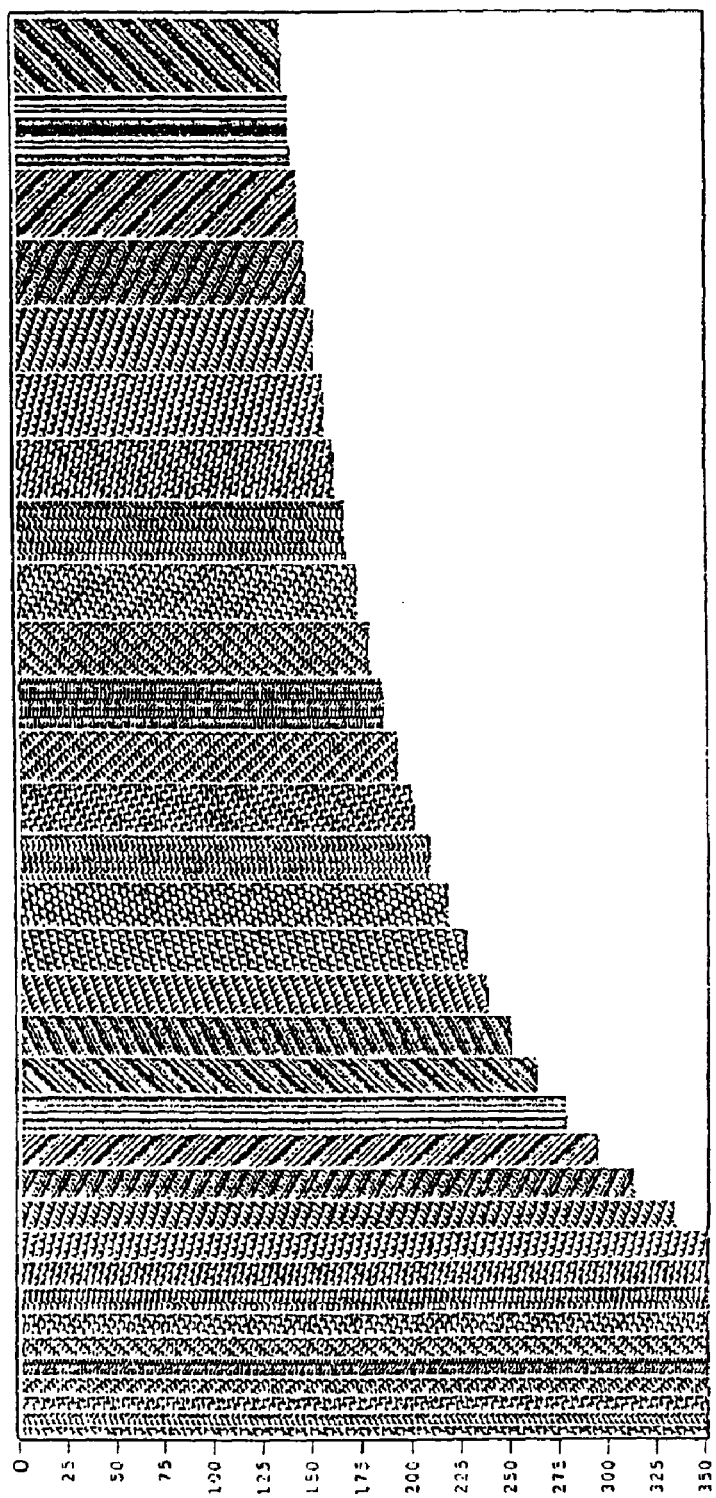
FIG. 4 shows a set of parallel sequences ΣA(k) generated from a circulating numerical sequence having a period length of 18 (symbolic sequence).
Figure 5:
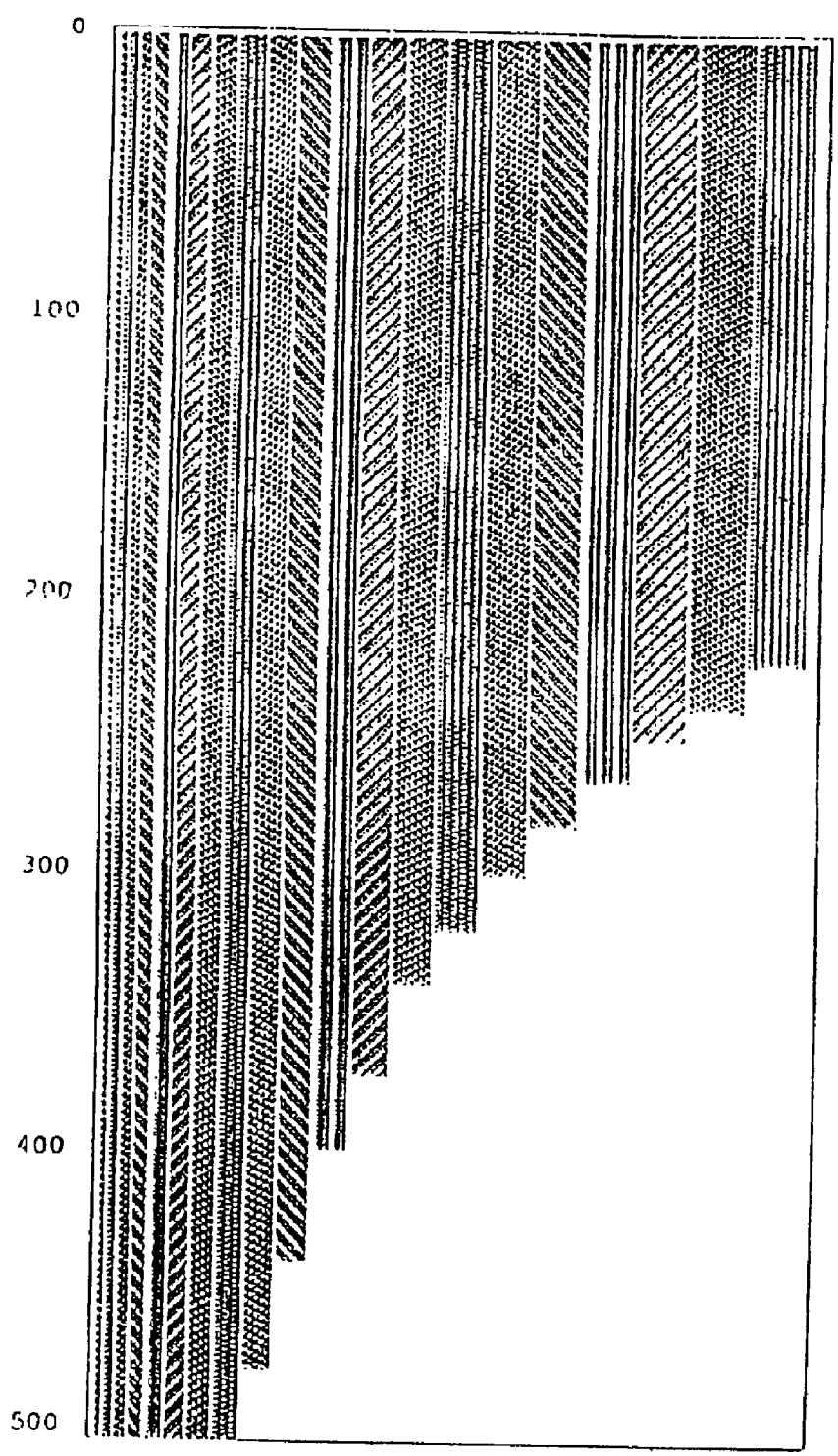
FIG. 5 shows a set of parallel sequences ΣA(k) generated from a circulating numerical sequence having a period length of 12 (symbolic sequence).

FIG. 4 represents a result obtained by processing a circulating numerical sequence of period length 18, and various patterns can be drawn according to the number k of a partial symbolic sequences to be fractionated. Various textile patterns can be designed by this pattern creating technology. FIG. 5 represents a processed result of a circulating numerical sequence of period length 12, and it is confirmed that different patterns from those of FIG. 4 can be made. According to this method, the complicated pattern shown in FIG. 3 and the regular patterns shown in FIGS. 4 and 5 can be designed by the same method. Further, various patterns that impart completely different impressions can be produced by changing the corresponding relationships of symbols and colors.

Figure 6:
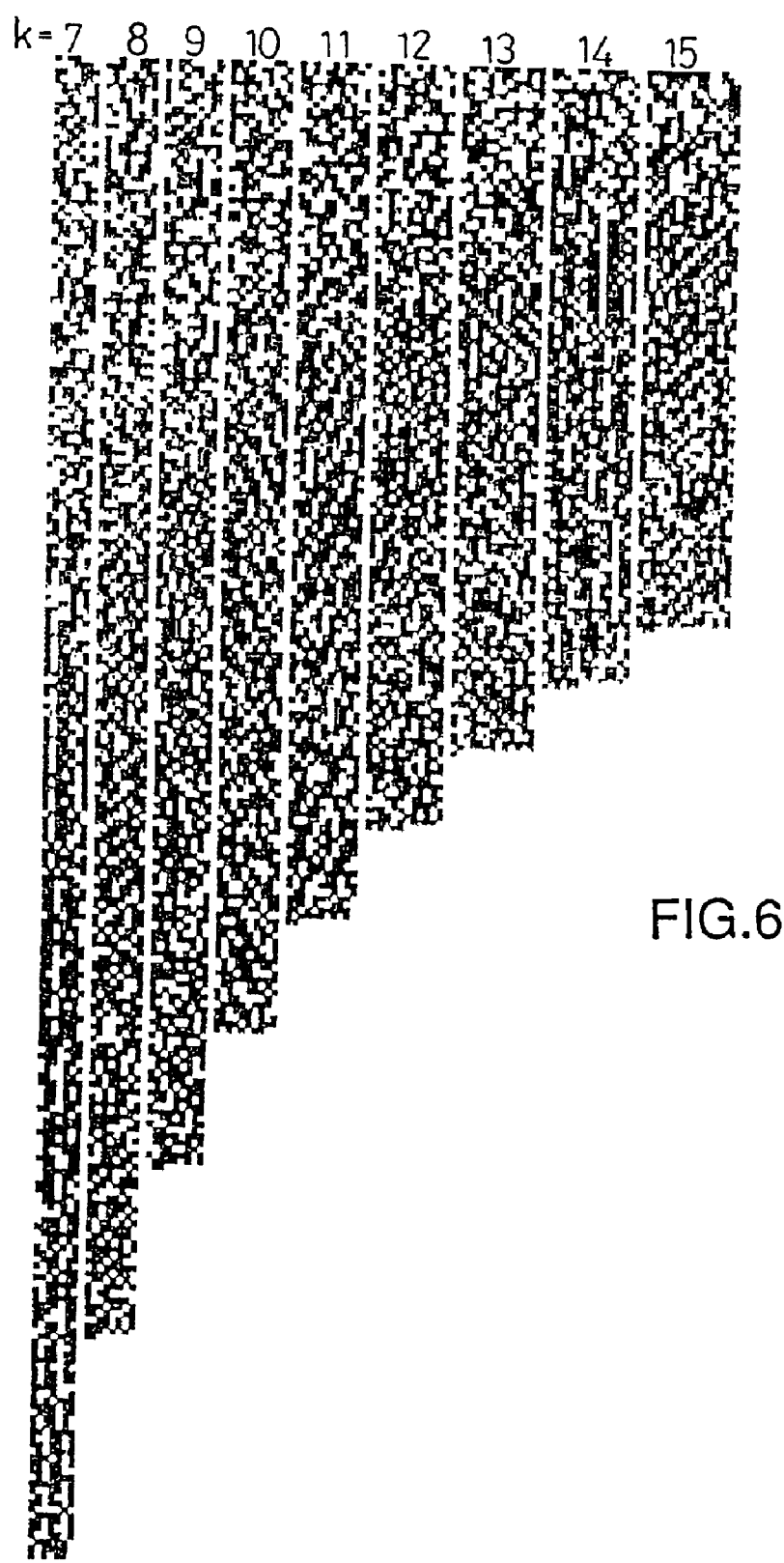
FIG. 6 shows a portion of the set of parallel sequences ΣA(k) generated from the amino acid sequence of the muscle protein myosin.
Figure 7:
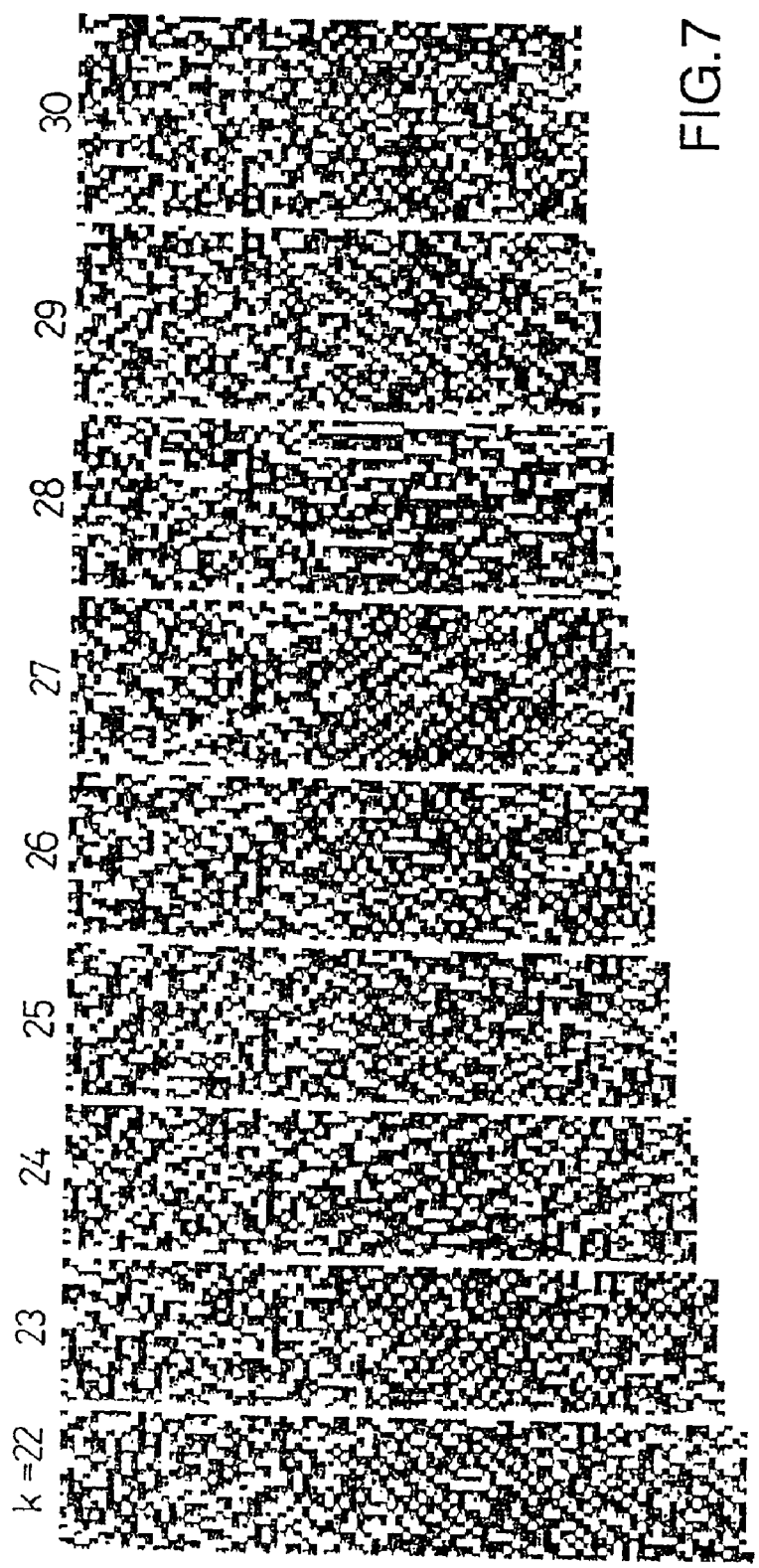
FIG. 7 shows another portion of the set of parallel sequences ΣA(k) generated from the amino acid sequence of the muscle protein myosin.
Figure 8:
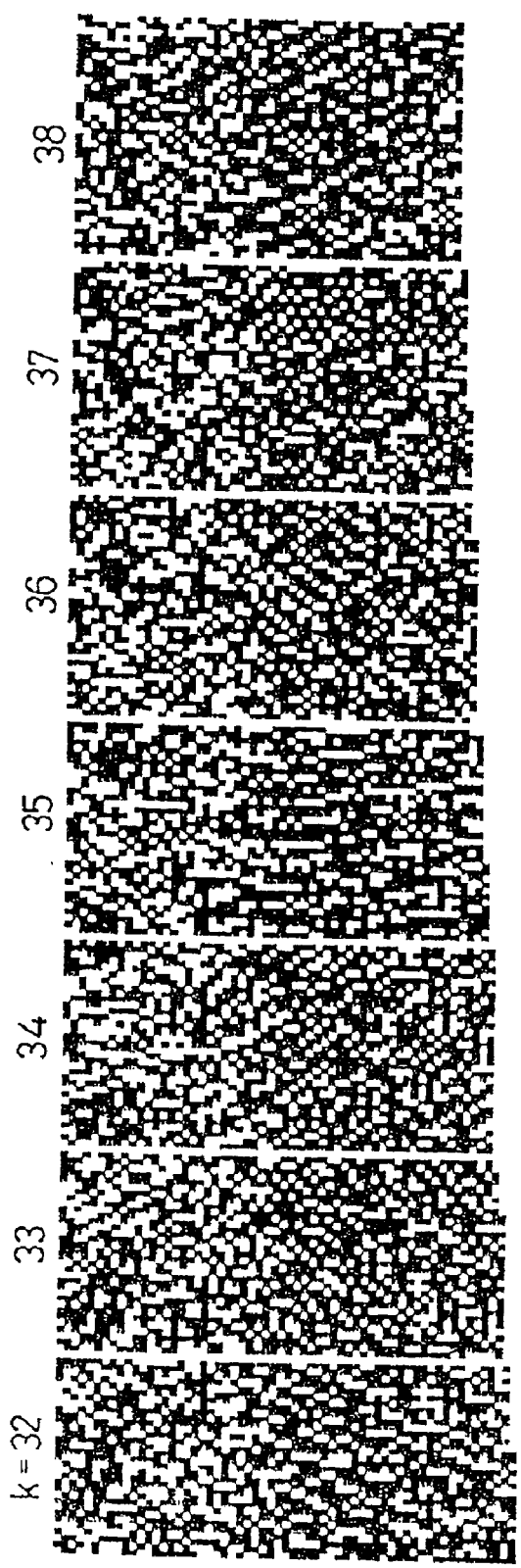
FIG. 8 shows another portion of the set of parallel sequences ΣA(k) generated from the amino acid sequence of the muscle protein myosin.

FIGS. 6 through 8 represent results obtained by processing a symbolic sequence which shows an amino acid sequence of a protein myosin of an adductor muscle of a scallop. In FIGS. 6 to 8, basic residues are shown in blue, polar residues are shown in green, acidic residues are shown in red, and hydrophobic residues are shown in yellow. In FIG. 6, a remarkable yellow longitudinal stripe appears in a parallel sequence in which k=7, and the existence of regularity having a period length of 7 was found. This regularity of hydrophobic residues having a period length of 7 corresponds to an α-helix, and by this method, the existence of an α-helix can be recognized and the existing position thereof can be identified. This α-helix is manifested as yellow longitudinal stripes in the parallel sequences in which k=7, 14, 28 and 35, and is manifested as yellow diagonal lines in the parallel sequences in which, for example, k=22, 27 and 29.

Figure 9:
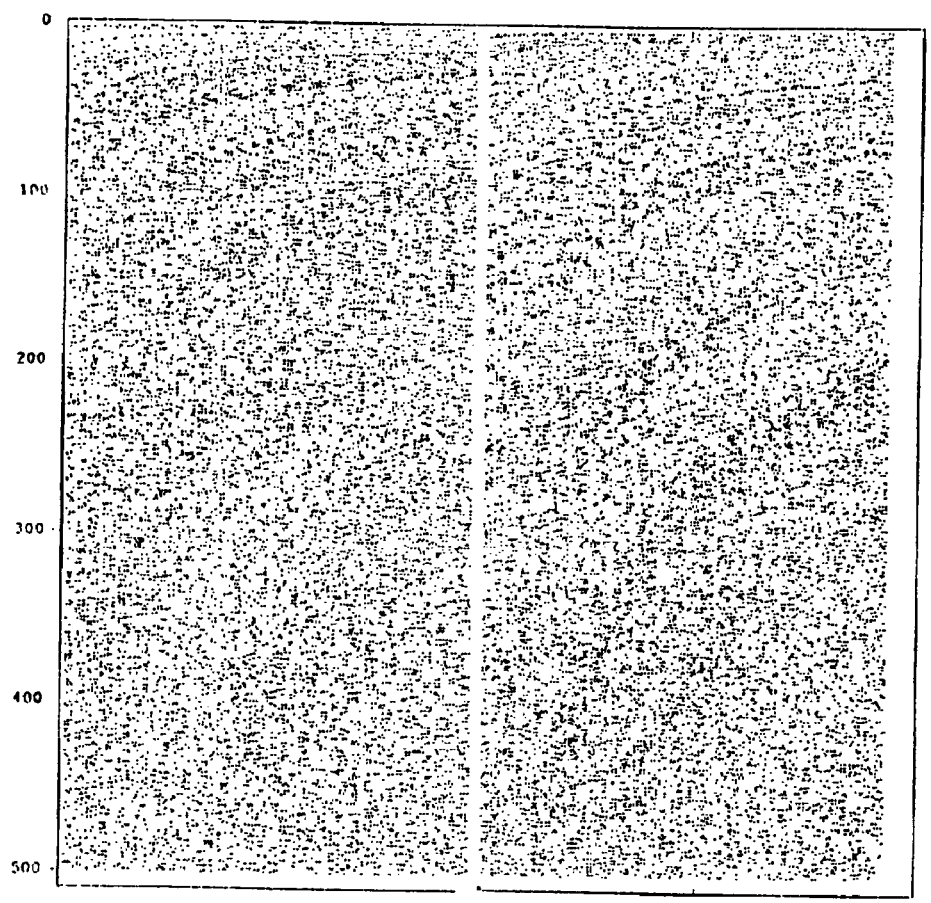
FIG. 9 shows the positions of the vowel 'O' appearing in 'Genji Monogatari'.

FIG. 9 represents an example expressing dots in positions where the vowel 'O' appears in the novel Genji Monogatari, and was prepared by applying the present method to a symbolic sequence of a row of vowels. The left side represents the analysis result of the chapter entitled Kiritsubo, and the right side represents the analysis result of the chapter entitled Hahakigi. There is manifested a characteristic that appears at a high frequency for the vowel 'O' within this specific portion of the document, and as low in other specific portions. By this method, extraction of characteristics in alphabet information becomes easy.

FIG. 10 schematically represents processing contents of a symbolic sequence $I_j$ (j=1 to 100).

When the period length of regularity to be extracted is known in advance, it will be easily recognized whether the regularity of the known period length k really exists, and in the case of existence, where it exists, by generating a parallel sequence A(k) in which partial symbolic sequences obtained by division into k fractions are parallel-positioned.

Even when the period length is not known, the regularity of the unknown period length is manifested at some location in the set of parallel sequences.

Figure 11:
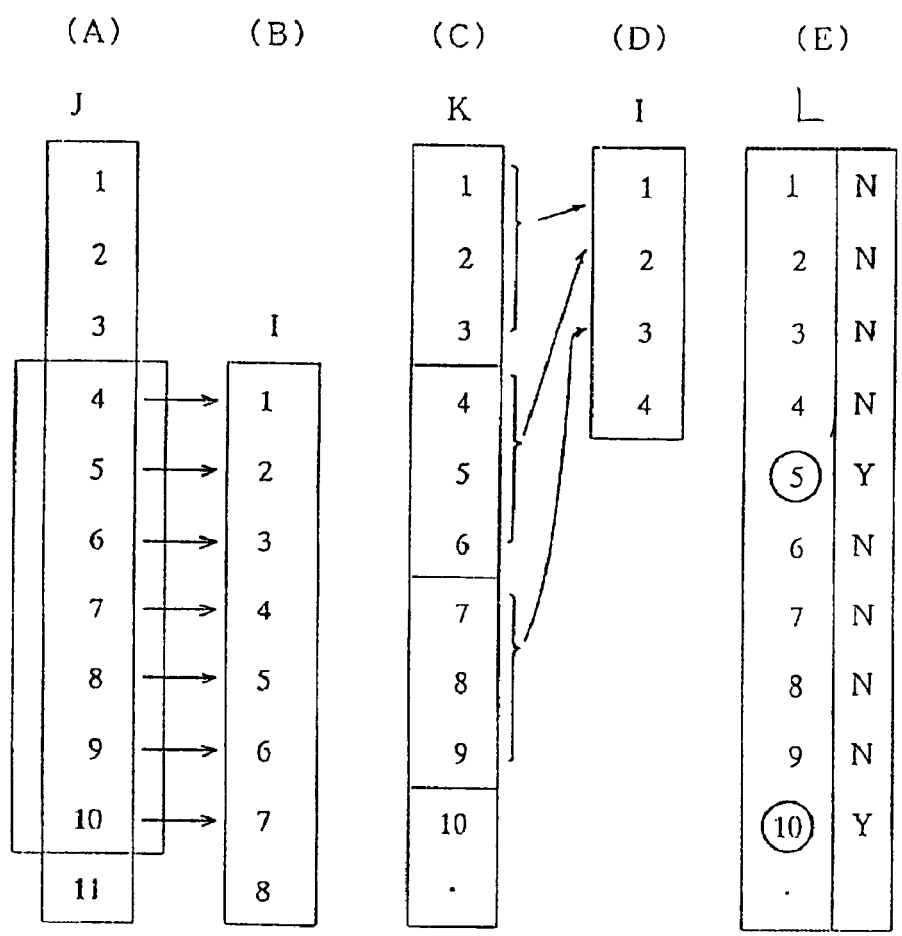
FIG. 11 explains pre-treatments for symbolic sequences.

FIG. 11 represents an example of pre-processing for a symbolic sequence that will be processed. When the portion of the symbolic sequence J shown under (A) is processed, the part shown under (B) will be the entire symbolic sequence I according to the present method. Further, when one symbol is specified by a combination of a plurality of symbols, this method is applied for the symbolic sequence identified by the combination of a plurality of symbols, for example, as shown in (C). In the alternative, one symbol can be obtained from symbols of order 123 in a symbolic sequence K. Then, one symbol can be obtained from symbols of order 234 in a symbolic sequence K, This procedure is repeated to effect conversion into one symbolic sequence I, and converted symbol I is processed using the present method, such as in the case of calculating a moving average. Further, as shown in (E), for a symbolic sequence existing in a symbolic sequence at specific period, a symbolic sequence of this period can first be extracted, and the present method is then applied to the extracted symbolic sequence.

Instead of this method, processing as exemplified in FIG. 12 may be effected. In this method, one symbol is extracted at every kq for a partial symbolic sequence of longitudinal direction. In the case shown in this drawing, the result is obtained by effecting the method and changing k to 2, 3, 4 . . . and q is fixed at 5. This result corresponds to the same result when a symbol of an order of 5·10·15 . . . is first extracted The extracted sequence is then separated into k partial symbolic sequences, and the resulting partial sequences are parallel-positioned to generate a parallel sequence. By this method, it is possible to manifest regularity further hidden in a symbolic sequence that is hidden in a symbolic sequence L (shown in (E) of FIG. 11).

When a set of parallel sequences of partial symbolic sequences is generated as described above, various methods can be utilized to express the result. For example, the symbol may be expressed by color, the symbol may be expressed by variations in color density and the symbol may be expressed by a character (two dimensional pattern). Further, the resulting lines and rows of symbols may also be expressed by sound. In this case, a chord is formed by an arrangement of symbols along the line direction, and an arrangement in a row direction is expressed by changing this chord over time. By this procedure, it becomes possible to recognize a characteristic existing in a symbolic sequence using sound.

The present invention is useful for analyzing various symbolic sequences, and useful for analyzing a nucleotide sequence of DNA, a nucleotide sequence of RNA, an amino acid sequence of a protein, a numerical sequence, an alphabet sequence, a sound sequence and the like. By this analysis, it becomes possible to identify an existing position of useful information and to extract useful information. Further, when this method is applied to two symbolic sequences, which can not be distinguished at a glance, characteristics are manifested, and the identity can be easily determined. In this sense, characteristics and regularity manifested using this method are not restricted to a repeating pattern having a certain period, and characteristics found in a distribution of appearing sequence are also manifested. Further, the increment r in the number of partial symbolic sequences is not necessarily required to be 1, and further, it is not required to be a constant number. By effecting this method according to k1, k2, k3 . . . distributing irregularly, characteristics existing in two or more symbolic sequences are manifested, and the identity is easily determined.

Figure 13:
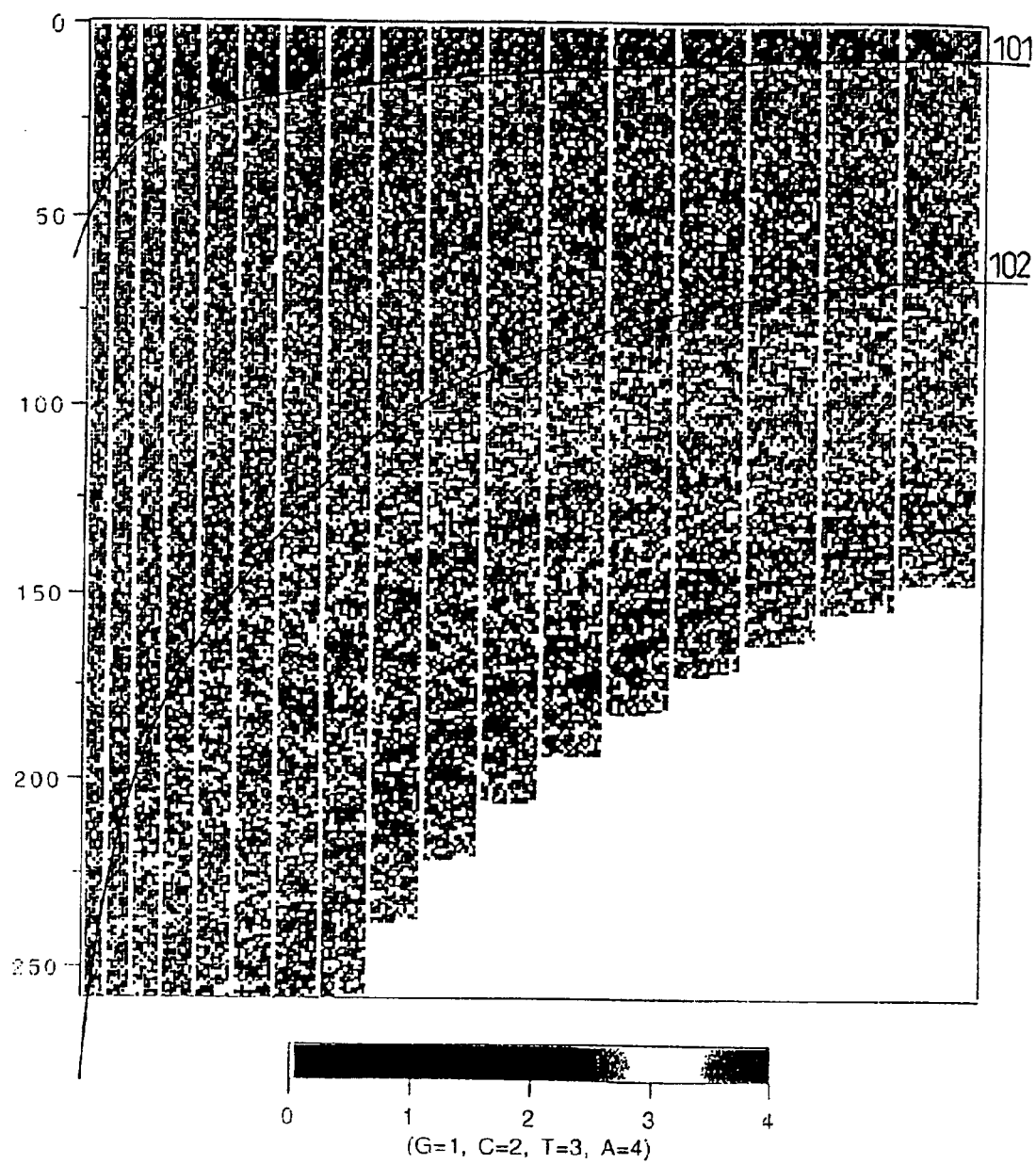
FIG. 13 shows a set of parallel sequences ΣA(k) generated from the cDNA sequence of a G protein β subunit.

FIG. 13 represents the analysis result of a cDNA sequence of a G protein β subunit, and represents the result when the set of parallel sequences ΣA(k) is generated by setting p equal to 5. In FIG. 13, GCTA are expressed by 4 colors and three different color zones are apparent.

The boundary 101 of the color zones corresponds approximately to the position of j=281, and the boundary 102 of the color zones corresponds approximately to the position of j=1303. In this case, it is known that a coding range exists within the range from j=281 to j=1303, and it is recognized that the coding range is easily identified using visual means in this method.

Figure 14:
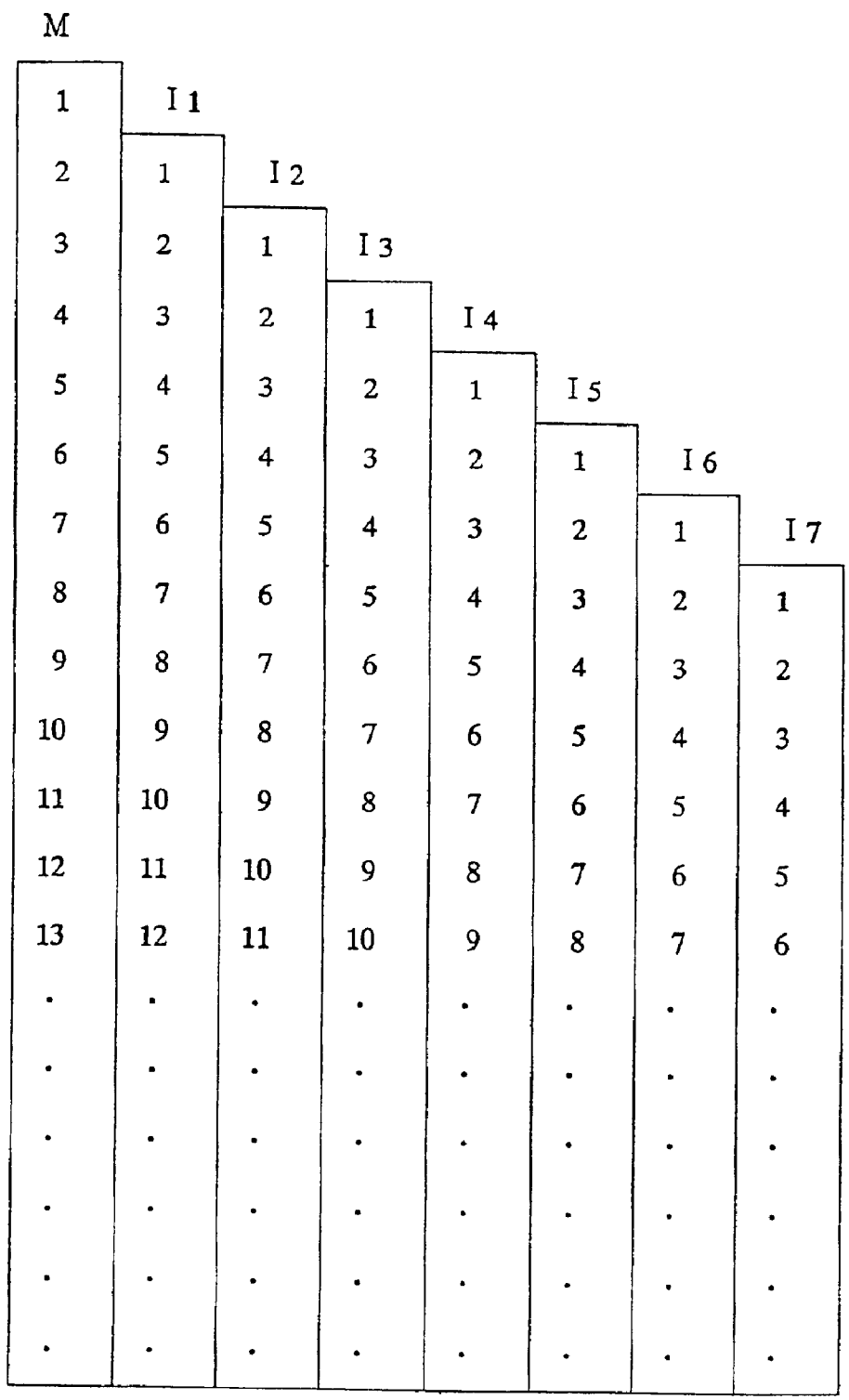
FIG. 14 represents extraction of symbolic sequence I from a symbolic sequence M by changing the initial point.

FIG. 14 represents a procedure for generating a symbolic sequence I from a one-dimensional symbolic sequence M by changing the initial point. For example, symbolic sequence 16 to be processed is a symbolic sequence obtained by extraction of M(6) and the following.

When the present invention is performed on symbolic sequences I1, I2, I3, I4 . . . thus extracted in order to generate the set of parallel sequences ΣA(k), a clear pattern may be visualized in the set of parallel sequences ΣA(k) corresponding to a specific I.

Figure 15:
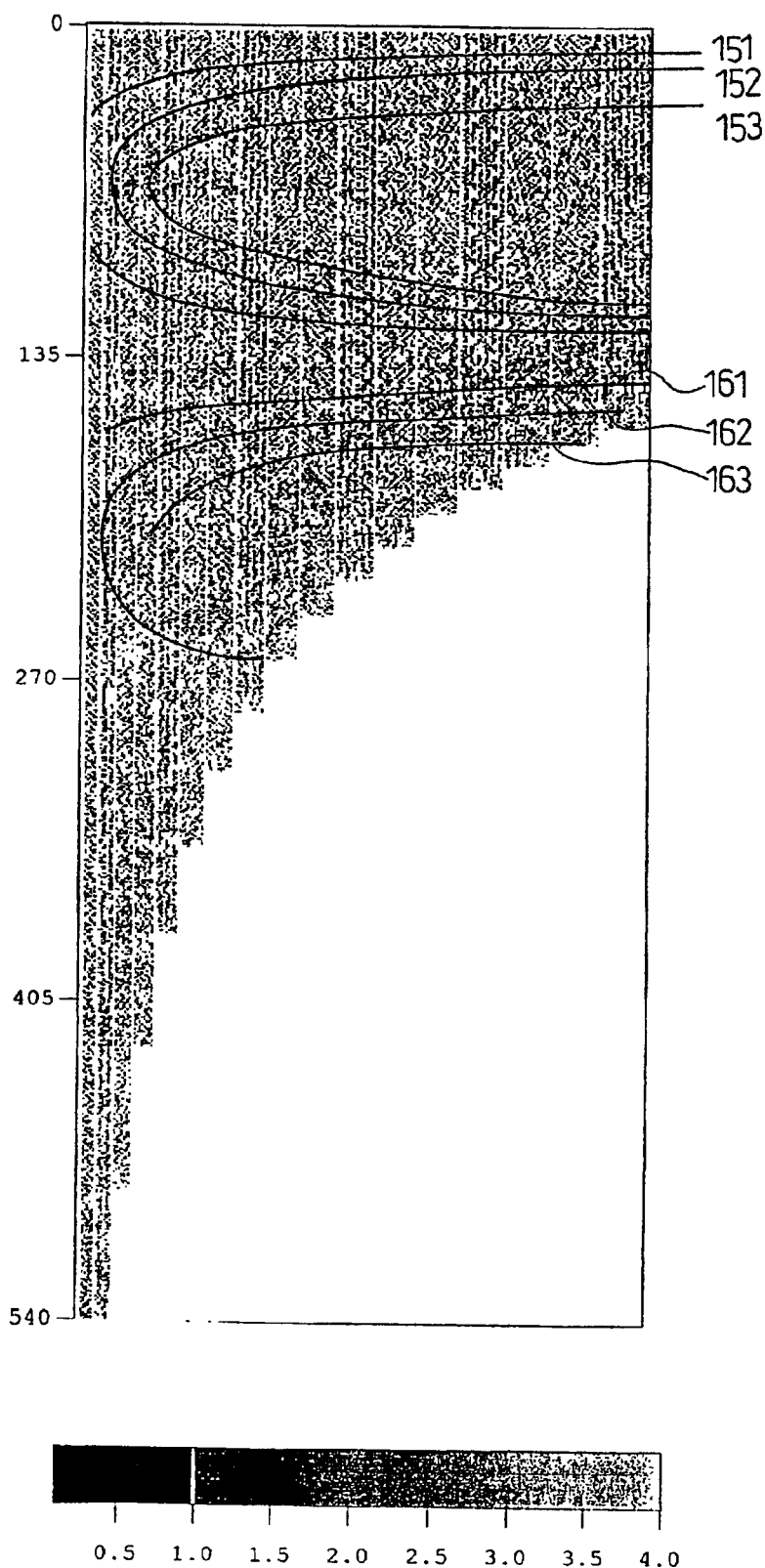
FIG. 15 shows an example in which a parabolic pattern appears in the set of parallel sequences ΣA(k) generated from a genomic DNA sequence of baker's yeast.

FIG. 15 represents one example thereof, in which a plurality of parabolic lines 151, 152, 153 . . . appear.

As a result of intensive study of this phenomenon, it has been recognized that the above-described line group appears when the initiation point of regularity coincides with the initiation point of the symbolic sequence to be processed. Consequently, it has been determined that the initiation point of regularity can be identified by utilizing the appearance of a line group.

Further, it was also determined that the appearance gap of a group of lines 151, 152, 153 . . . and other group of lines 161, 162, 163 . . . corresponds to regularity of an extremely long period, and it has also been recognized that the regularity of an extremely long period can be recognized by utilizing a line group.

Figure 17:
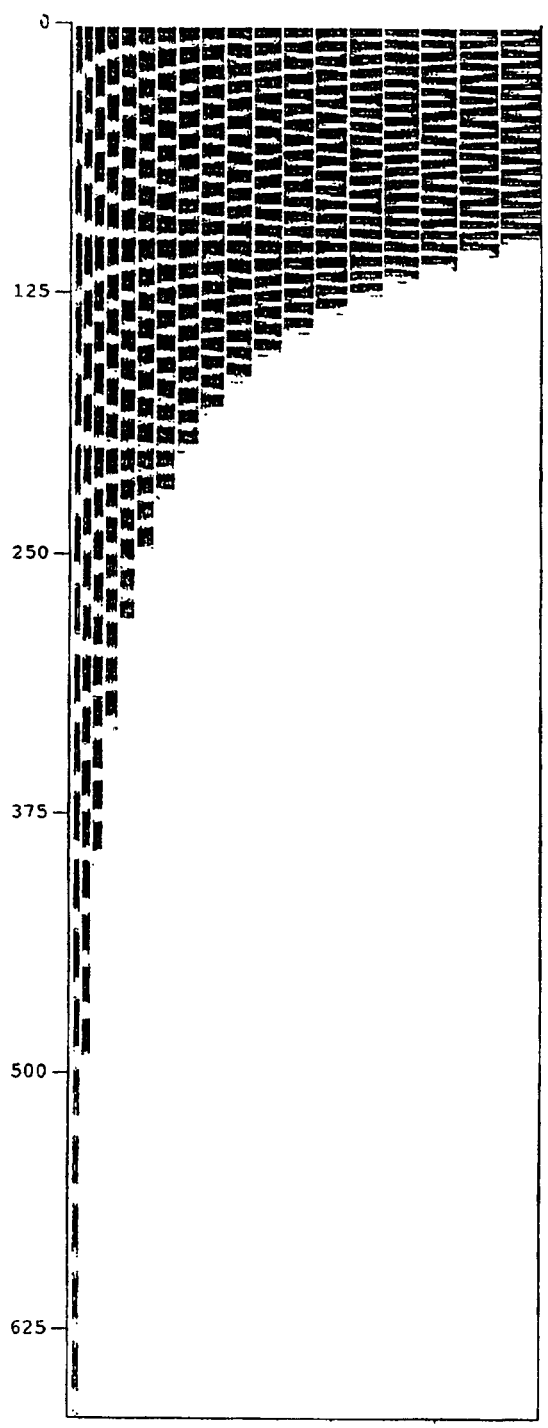
FIG. 17 shows a set of parallel sequences ΣA(k) generated from a circulating sequence having a period length of 100.
Figure 17:
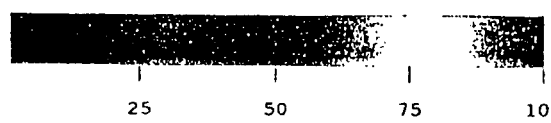

It has been recognized that the above-described pattern also appears by alternately reversing the sequential direction of the partial symbolic sequences in a lateral direction (reciprocal positioning pattern). FIG. 16 represents a positional relationship for generating parallel sequences A(k) by alternately reversing the sequential direction of the partial symbolic sequences along the lateral direction. FIG. 17 represents an example in which a circulating sequence having a period of 100 is converted into a set of parallel sequences ΣA(k) having the positional relationship as shown in FIG. 16, and a clear line group appeared.

The above-described explanations are only some specific examples and the present invention can be used in various ways within the attached claims.

What is claimed is:

1. An apparatus for expressing a characteristic in alphanumeric data comprising at least a first alphanumeric data representation and a second alphanumeric data representation, comprising:
   a computer processor arranged and constructed to execute instructions to:
   (i) convert a single linear sequence of the alphanumeric data into at least a first matrix of alphanumeric data, a second matrix of alphanumeric data and a third matrix of alphanumeric data, the first matrix having X columns, the second matrix having Y columns and the third matrix having Z columns, wherein X, Y, Z are integers that are equal or greater than 2 and X, Y and Z are each different integers,
   (ii) assign a first color to the first alphanumeric data representation and
   (iii) assign a second color to the second alphanumeric data representation, wherein the first color and the second color are different from each other, and
   means for visually displaying the first, second and third matrices in a proximal relationship.

2. An apparatus as in claim 1, wherein the visual display means displays the at least first, second and third matrices in a side-by-side relationship.

3. An apparatus as in claim 1, wherein Y equals X+r and Z equals X+2 r, and wherein r is an integer.

4. An apparatus as in claim 1, wherein the visual display means comprises a printer.

5. An apparatus as in claim 1, wherein the alphanumeric data represents nucleotides and the visual display means comprises means for visually displaying 4 different colors that are representative of the nucleotides.

6. An apparatus as in claim 1, wherein the alphanumeric data represents amino acids and the visual display means comprises means for visually displaying a plurality of different colors that are representative of the amino acids.

7. An apparatus for identifying a repeating sub-sequence within a single linear sequence of alphanumeric data comprising at least a first alphanumeric data representation and a second alphanumeric data representation, comprising:
   means for converting the single linear sequence of the alphanumeric data into at least a first matrix of alphanumeric data, a second matrix of alphanumeric data and a third matrix of alphanumeric data, the first matrix having X columns, the second matrix having Y columns and the third matrix having Z columns, wherein X, Y, Z are integers that are equal or greater than 2 and X, Y and Z are each different integers,
   means for assigning a first color to the first alphanumeric data representation,
   means for assigning a second color to the second alphanumeric data representation, wherein the first color and the second color are different from each other, and
   means for visually displaying the first, second and third matrices in a side-by-side relationship.

8. An apparatus as in claim 7, wherein Y equals X+r and Z equals X+2r, and wherein r is an integer.

9. An apparatus as in claim 7, wherein the alphanumeric data represents nucleotides and the visual display means comprises means for visually displaying 4 different colors that are representative of the nucleotides.

10. An apparatus as in claim 7, wherein the alphanumeric data represents amino acids and the visual display means comprises means for visually displaying a plurality of different colors that are representative of the amino acids.

11. An apparatus for expressing at least one characteristic existing in a sequence of symbols $I_1, I_2, \ldots I_m$, wherein m comprises a positive integer, comprising:
   memory arranged and constructed to store the sequence of symbols $I_1, I_2, \ldots, I_m$;
   a processor arranged and constructed to generate parallel sequences A(k) in the form of a matrix X having m matrix elements X(u,v) arranged in n rows and k columns using the sequence of symbols $I_1, I_2, \ldots, I_m$ stored in the memory by assigning an element of the sequence of symbols $I_1, I_2, \ldots, I_m$ to each matrix element X(u,v), wherein $X(u,v)=I_j$ and one relationship is satisfied from the group consisting of:
   (a) $u=\lceil j \div k \rceil$ and $v=j-(\lceil j \div k \rceil -1) \cdot k$ for each value of j satisfying $1 \leq j \leq m$,
   (b) $u=\lceil j \div k \rceil$ and $v=j-(\lceil j \div k \rceil -1) \cdot k$ for each value of j satisfying $1 \leq j \leq m$ and $\lceil j \div k \rceil$ having a value which comprises an odd integer, and
   $u=\lceil j \div k \rceil$ and $v=(\lceil j \div k \rceil \cdot k)-j+1$ for each value of j satisfying $1 \leq j \leq m$ and $\lceil j \div k \rceil$ having a value which comprises an even integer, (c) u=⌈j÷k⌉ and v=(⌈j÷k⌉·k)−j+1 for each value of j satisfying 1≦j≦m, and (d) u=⌈j÷k⌉ and v=(⌈j÷k⌉·k)−j+1 for each value of j satisfying 1≦j≦m and ⌈j÷k⌉ having a value which comprises an odd integer, and u=⌈j÷k⌉ and v=j−(⌈j÷k⌉−1)·k for each value of j satisfying 1≦j≦m and ⌈j÷k⌉ having a value which comprises an even integer, wherein, for each relationship (a)–(d), k comprises an integer satisfying k≧2, n=⌈m÷k⌉, ⌈m÷k⌉ comprises the smallest positive integer having a value that is greater than or equal to the value of m÷k, and ⌈j÷k⌉ comprises the smallest positive integer having a value that is greater than or equal to the value of j÷k;

the processor being further arranged and constructed to generate at least three matrices selected from matrices $X_1, X_2, \ldots, X_p$ by further parallel-positioning of parallel sequences A(p), A(p+r), A(p+2r), A(p+3r), ... converted by changing k to p, p+r, p+2r, p+3r, ..., wherein p comprises an integer satisfying p≦(m÷2), and r comprises an integer; and visual expression means for visually displaying the at least three matrices using different color hues, color lightness or color saturation, wherein the visual expression means visually displays the at least three matrices in a proximal relationship.

12. An apparatus as in claim 11, wherein the processor is further arranged and constructed to:

(a) extract symbols sequentially from a sequence of symbols $M_1, M_2, \ldots, M_u$, wherein u comprises a positive integer that will generate the sequence of symbols $I_1, I_2, \ldots, I_m$;

(b) generate the set of parallel sequences A(k) from the extracted sequence of symbols $I_1, I_2, \ldots, I_m$; and repeat steps (a) and (b) while shifting an initiation point within the sequence of symbols $M_1, M_2, \ldots, M_u$ from which the sequence of symbols $I_1, I_2, \ldots, I_m$ is extracted.

13. An apparatus as in claim 11, wherein the processor is further arranged and constructed to:

sequentially remove symbols from a sequence of symbols $L_1, L_2, \ldots, L_t$ at an interval q to form the sequence of symbols $I_1, I_2, \ldots, I_m$, wherein t has a value ≧(m·q).

14. An apparatus as in claim 11, wherein the sequence of symbols $I_1, I_2, \ldots, I_m$ represents nucleotides and the visual expression means comprises means for visually displaying 4 different colors that are representative of the nucleotides.

15. An apparatus as in claim 11, wherein the sequence of symbols $I_1, I_2, \ldots, I_m$ represents amino acids and the visual expression means comprises means for visually displaying a plurality of different colors that are representative of the amino acids.

16. An apparatus for expressing at least one characteristic existing in a sequence of symbols $I_1, I_2, \ldots, I_m$, wherein m comprises a positive integer and the symbols $I_1, I_2, \ldots, I_m$ are depicted using a first set of visual representations, comprising:

means for storing the sequence of symbols $I_1, I_2, \ldots, I_m$;

means for generating a parallel sequence A(k) in the form of a matrix X having m matrix elements X(u,v) arranged in n rows and k columns using the sequence of symbols $I_1, I_2, \ldots, I_m$ stored in the storing means by assigning an element of the sequence of symbols $I_1, I_2, \ldots, I_m$ to each matrix element X(u,v), wherein X(u,v)=$I_j$ and one relationship is satisfied from the group consisting of:

(a) u=⌈j÷k⌉ and v=j−(⌈j÷k⌉−1)·k for each value of j satisfying 1≦j≦m, (b) u=⌈j÷k⌉ and v=j−(⌈j÷k⌉−1)·k for each value of j satisfying 1≦j≦m and ⌈j÷k⌉ having a value which comprises an odd integer, and u=⌈j÷k⌉ and v=(⌈j÷k⌉·k)−j+1 for each value of j satisfying 1≦j≦m and ⌈j÷k⌉ having a value which comprises an even integer, (c) u=⌈j÷k⌉ and v=(⌈j÷k⌉·k)−j+1 for each value of j satisfying 1≦j≦m, and (d) u=⌈j÷k⌉ and v=(j÷k⌉·k)−j+1 for each value of j satisfying 1≦j≦m and ⌈j÷k⌉ having a value which comprises an odd integer, and u=⌈j÷k⌉ and v=j−(⌈j÷k⌉−1)·k for each value of j satisfying 1≦j≦m and ⌈j÷k⌉ having a value which comprises an even integer, wherein, for each relationship (a)–(d), k comprises an integer satisfying k≧2, n=⌈m÷k⌉, ⌈m÷k⌉ comprises the smallest positive integer having a value that is greater than or equal to the value of m÷k and ⌈j÷k⌉ comprises the smallest positive integer having a value that is greater than or equal to the value of j÷k;

means for generating at least three matrices selected from matrices $X_1, X_2, \ldots, X_p$ by further parallel-positioning of parallel sequences A(p), A(p+r), A(p+2r), A(p+3r), ... converted by changing k to p, p+r, p+2r, p+3r, ..., wherein p comprises an integer satisfying p≦(m÷2), and r comprises an integer;

means for converting the symbols $I_1, I_2, \ldots, I_m$ to a second set of visual representations $S_1, S_2, \ldots, S_m$, the second set of visual representations differing from the first set of visual representations and comprising a plurality of different colors, color hues, color lightness or color saturation; and means for visually displaying the at least three matrices $X_1, X_2, \ldots, X_p$ of symbols $S_1, S_2, \ldots, S_m$.

17. An apparatus as in claim 16, further comprising:

means for sequentially removing symbols from a sequence of symbols $L_1, L_2, \ldots, L_t$ at an interval q to form the sequence of symbols $I_1, I_2, \ldots, I_m$ wherein t has a value≧(m·q).

18. An apparatus as in claim 16, wherein the visually displaying means displays the at least three matrices of symbols $S_1, S_2, \ldots, S_m$ in a side-by-side relationship.

19. An apparatus as in claim 16, wherein the sequence of symbols $I_1, I_2, \ldots, I_m$ represents nucleotides and the visual display means comprises means for visually displaying 4 different colors that are representative of the nucleotides.

20. An apparatus as in claim 16, wherein the sequence of symbols $I_1, I_2, \ldots, I_m$ represents amino acids and the visual display means comprises means for visually displaying a plurality of different colors that are representative of the amino acids.

* * * * *